United States Patent [19]
Terren et al.

[11] Patent Number: 5,972,378
[45] Date of Patent: *Oct. 26, 1999

[54] AQUEOUS COMPOSITION CONTAINING NONIONIC LIPID VESICLES AND AT LEAST ONE UNCOATED PIGMENT DISPERSED IN AN AQUEOUS PHASE, PROCESS FOR PREPARATION AND USE THEREOF

[75] Inventors: Nadia Terren, Chevilly Larue; Fabienne Bouchard, Villejuif; Jacques Michelet, Champlan, all of France

[73] Assignee: L'Oreal, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/779,002

[22] Filed: Jan. 3, 1997

[30] Foreign Application Priority Data

Jan. 3, 1996 [FR] France ................................ 96 00030

[51] Int. Cl.$^6$ .............................. A61K 9/127; A61K 7/00
[52] U.S. Cl. ......................... 424/450; 424/401; 424/63; 424/70.6; 514/844; 514/937
[58] Field of Search .................................. 424/450, 401, 424/63, 70.6; 514/844, 937

[56] References Cited

U.S. PATENT DOCUMENTS

| | | |
|---|---|---|
| 4,608,211 | 8/1986 | Handjani et al. . |
| 4,772,471 | 9/1988 | Vanlergerghe et al. . |
| 4,897,308 | 1/1990 | Vanlergerghe et al. . |
| 5,021,200 | 6/1991 | Vanlergerghe et al. . |
| 5,268,180 | 12/1993 | Morancais et al. . |
| 5,443,840 | 8/1995 | Morancais et al. . |
| 5,451,254 | 9/1995 | Andrean et al. . |
| 5,498,420 | 3/1996 | Mentrup Edgar et al. . |

FOREIGN PATENT DOCUMENTS

| | | |
|---|---|---|
| 0 485 251 | 5/1992 | European Pat. Off. . |
| 0 509 338 | 10/1992 | European Pat. Off. . |
| 0 523 418 | 1/1993 | European Pat. Off. . |
| 0 537 092 | 4/1993 | European Pat. Off. . |
| 0 582 503 | 2/1994 | European Pat. Off. . |
| 2 315 991 | 1/1977 | France . |
| 2 681 329 | 3/1993 | France . |
| 2136762 | 9/1984 | United Kingdom . |
| WO 93/15708 | 8/1993 | WIPO . |

OTHER PUBLICATIONS

Handjain International J. of Cosmetic Science 1, pp. 303–314, 1979.
*Soap, Cosmetics, Chemical Specialties*. Abate, Kenneth, "Non–phospholipid Liposomes in Cosmetics," 65(5):37–40, May, 1993.
English language Derwent abtract of EPA–0 523 418.
English language Derwent abstract of EPA–0 537 092.
English language Derwent abstract of EPA–0 582 503.

*Primary Examiner*—Gollamudi S. Kishore
*Attorney, Agent, or Firm*—Finnegan, Henderson, Farabow, Garrett & Dunner, L.L.P.

[57] ABSTRACT

Compositions comprising an aqueous dispersion of lipid vesicles having an aqueous core, wherein the dispersion comprises at least one uncoated pigment dispersed in the aqueous phase and wherein the lipid vesicles with an aqueous core and a lipid membrane formed from at least one fatty acid ester, these compositions being stable, of homogeneous color and containing no or virtually no lumps of pigment, and a process for dispersing a filler in an oil-in-water dispersion of lipid vesicles by means of a high-pressure homogenizer.

38 Claims, No Drawings

AQUEOUS COMPOSITION CONTAINING NONIONIC LIPID VESICLES AND AT LEAST ONE UNCOATED PIGMENT DISPERSED IN AN AQUEOUS PHASE, PROCESS FOR PREPARATION AND USE THEREOF

The present invention relates to compositions comprising an aqueous dispersion containing at least one uncoated pigment which is dispersed in an aqueous phase and lipid vesicles with an aqueous core based on fatty acid ester. The present invention also relates to a process for their preparation and to their cosmetic or dermatological use.

It is known that certain amphiphilic lipids possess the property of forming mesomorphous phases, whose state of organization is intermediate between the crystalline and the liquid state, and that, among these, some are capable of swelling in the presence of an aqueous solution to form a lamellar phase and then, after stirring, to form vesicles or spherules with an aqueous core which are dispersed in an aqueous phase. These vesicles are formed by a membrane containing substantially concentric leaflets including one or more multimolecular, preferably bimolecular, layers encapsulating an aqueous phase.

The abovementioned vesicles with an aqueous core (encapsulating an aqueous phase) may be prepared by many processes. According to a first process, which is described, for example, by Bangham et al. (J. Mol. Bio., 13, 1965—pages 238 to 262), the disclosure of which is specifically incorporated herein by reference, the lipid phase is dissolved on the walls of a flask by evaporation of the solvent, the phase to be encapsulated is introduced onto the lipid film and the mixture is stirred mechanically until the dispersion of vesicles with the desired size is obtained. A dispersion of vesicles encapsulating an aqueous phase is thus obtained, the encapsulated aqueous phase and the dispersing aqueous phase being identical.

According to a second so-called "lipid co-fusion" process, which is described, for example, in FR-A-2,315,991, the disclosure of which is specifically incorporated herein by reference, the lipid phase is prepared by mixing the amphiphilic lipid(s) and the possible additives, at a temperature at which the mixture is molten, if the mixture is not liquid at room temperature. A lamellar phase is formed by introduction of the aqueous phase to be encapsulated. The lamellar phase is then dispersed in the form of vesicles, using an ultra-disperser, a homogenizer or ultrasound, in a dispersing aqueous phase. In a variant of this process, the formation of the lamellar phase does not constitute a separate stage of the process.

The vesicles obtained by these two processes are generally of "multileaflet" type. To obtain vesicles of "monoleaflet" type, the teachings of FR-A-2,543,018 may be used, the disclosure of which is specifically incorporated herein by reference.

Irrespective of the process used, vesicles with an aqueous core are obtained in the form of a dispersion in an aqueous phase.

In a known manner, amphiphilic lipid vesicles with an aqueous core may contain cosmetic or pharmaceutical active agents, either in the encapsulated aqueous phase if the active agents are water-soluble, or in the lipid membrane if they are fat-soluble. Active agents may also be present in the dispersing aqueous phase. The amphiphilic lipids used to produce the vesicles are preferably lipids having the general formula:

X—Y in which X represents a hydrophilic group and Y represents a lipophilic group. The amphiphilic lipids may preferably be ionic lipids, for which the X group is ionic, or nonionic lipids, for which the X group is nonionic.

In a known manner, mixtures of ionic amphiphilic lipids, mixtures of nonionic amphiphilic lipids and mixtures of these two types of lipids may be used for the manufacture of vesicles with an aqueous core.

Nonionic lipid vesicles with an aqueous core, containing polyol esters of $C_5$–$C_{17}$ fatty acids, have been proposed in application FR-A-2,694,884, the disclosure of which is incorporated herein by reference.

Dispersions of nonionic lipid vesicles with an aqueous core, based on α-butylglucoside esters of fatty acid, have also been proposed in unpublished patent application Ser. No. 95/02199, the disclosure of which is specifically incorporated herein by reference.

These lipid vesicles with an aqueous core based on fatty acid esters are particularly advantageous in cosmetics and in dermatology, insofar as they display a good level of encapsulation of water-soluble or liposoluble active agents, good degradability under the action of the pH of the skin or by skin enzymes, and good stability in water.

They are particularly suitable for the production of oil-in-water emulsions such as creams, milks, lotions or sera to care for the skin and/or the scalp as agents for dispersing the oily phase in the aqueous phase.

For the manufacture of foundations, tinted creams and complexion correctors or enhancers, pigments such as iron oxides or titanium oxides are generally used in order to provide the covering effect and/or the coloring effect on the face.

One aim of the present invention is to be able to produce compositions in the form of an oil-in-water dispersion of lipid vesicles with an aqueous core based on fatty acid esters and containing uncoated pigments in the dispersing aqueous phase.

Hitherto, compositions containing a dispersion of lipid vesicles with an aqueous core of this type could only contain, in the dispersing aqueous phase, pigments coated with silicones, fluoro compounds or amino acids. Such compositions are described in European patent application EP-A-582,503.

The reason for this is that the dispersion of uncoated pigments in an aqueous phase, in which the lipid vesicles with an aqueous core based on fatty acid esters are also dispersed, destabilizes the emulsion. Their use leads to the formation of lumps of pigment which ruin the cosmetic and aesthetic qualities of the final product, i.e., heterogeneous color, separation of the phases and even inability to produce the dispersion.

The use of coated pigments in oil-in-water dispersions of lipid vesicles with an aqueous core comprising a fatty acid ester also poses a certain number of manufacturing problems. The lower wettability of coated pigments in the fatty phase and in the aqueous phase has a negative impact on the homogeneity and the stability of the emulsion. Their dispersion requires more vigorous and longer stirring using a standard homogenizer of turbomixer type.

The Inventors have discovered, surprisingly, that uncoated pigments can be incorporated into the aqueous phase of a dispersion of lipid vesicles with an aqueous core containing fatty acid esters without the drawbacks stated above, using a high-pressure homogenizing device. The oil-in-water dispersions thus obtained are stable, have a homogeneous color and contain no or virtually no lumps of pigment.

One subject of the invention is thus novel compositions in the form of an oil-in-water dispersion comprising, at least in the aqueous phase, an uncoated pigment and lipid vesicles having an aqueous core whose membrane is formed from at least one fatty acid ester.

Another subject of the invention is a process for dispersing at least one filler in an oil-in-water dispersion of lipid vesicles, by high-pressure homogenization, in particular an uncoated pigment in an oil-in-water dispersion of lipid vesicles having an aqueous core whose membrane is formed from at least one fatty acid ester.

Another subject is a process for preparing the compositions of the invention.

The compositions according to the invention are characterized in that they preferably comprise an oil-in-water dispersion comprising lipid vesicles having an aqueous core whose lipid membrane is formed from at least one fatty acid ester and at least one uncoated pigment which is dispersed in the dispersing aqueous phase.

The compositions according to the invention are more particularly oil-in-water dispersions in which the vesicles with an aqueous core act as an agent for dispersing droplets of oil in the dispersing aqueous phase.

The term pigment is understood to refer to any inorganic or organic pulverulent filler which is insoluble in an oil-in-water dispersion and has coloring and/or covering properties on keratinous material, in particular the skin.

The fatty acid esters constituting the membrane of the lipid vesicles with an aqueous core of the invention are preferably chosen from the group formed by:
(i) polyol esters of fatty acid, which may or may not be polyoxyethylenated, and
(ii) α-butylglycoside esters of fatty acid.

The polyol esters of fatty acid are preferably chosen from mixtures of esters of at least one polyol selected from: polyethylene glycol containing from 1 to 60 ethylene oxide units, sorbitan, sorbitan carrying from 2 to 60 ethylene oxide units, glycerol carrying from 2 to 30 ethylene oxide units, polyglycerols containing from 2 to 15 glycerol units, sugars, glucoses carrying from 2 to 30 ethylene oxide units, and at least one fatty acid containing a linear or branched, saturated or unsaturated $C_5$–$C_{17}$ alkyl chain, wherein the number of alkyl chains per polyol group ranges from 1 to 10.

The polyol esters of $C_5$–$C_{17}$ fatty acids which are particularly preferred are those corresponding to the formula:

 (I)

wherein n is a random value which may contain various proportions of esters for which n=1, n=2, n=3, n=4, etc. This is also the case for esters containing several alkyl chains in their lipophilic part, such as cocoates, which contain $C_5$–$C_{17}$ alkyl chains, or isostearates in which the $C_{17}$ alkyl chains are a complex mixture of isomeric forms. This is also the case for products comprising mixtures of mono-, di-, tri- or polyesters of the same polyol.

Among the commercial products which can be used according to the invention and which have the structure of a mixture of polyol esters of $C_5$–$C_{17}$ fatty acid as defined above, mention may be made of:
partial esters of sorbitan (or sorbitol anhydride) and of fatty acid, sold under the trade names "Span 20, 40, 60 and 80" by the company "ICI";
sorbitan isostearate, sold under the trade name "SI 10 R Nikkol" by the company "Nikko";
sorbitan stearate carrying 4 ethylene oxide units, sold under the name "Tween 61" by the company "ICI";

polyethylene glycol stearate containing 8 ethylene oxide units, sold under the name "MYR J 45" by ICI;
the polyethylene glycol monostearate of formula

wherein n is equal to 4, sold under the name "MYS 4" by the company "Nikko";
polyethylene glycol stearate of molecular weight 400, of chemical grade or of biotechnological grade, sold by the company "Unichema";
diglyceryl stearate carrying 4 ethylene oxide units, sold under the name "Hostacerine DGS" by the company "Hoechst";
tetraglyceryl stearate, sold under the name "Tetraglyn 1S" by the company "Nikko";
diglyceryl isostearate, sold by the company "Solvay";
diglyceryl distearate, sold under the name "Emalex DSG 2" by the company "Nihon";
sucrose mono-, di- and tripalmitostearate, sold under the names "F50, F70, F110 and F160 Crodesta" by the company "Croda";
the mixture of sucrose mono- and dipalmitostearate sold under the name "Grilloten PSE 141 G" by the company "Grillo";
the mixture of sucrose stearate and sucrose cocoate, sold under the name "Arlatone 2121" by the company "ICI";
methylglucose distearate carrying 20 ethylene oxide units, sold under the name "Glucam E20 distearate" by the company "Amerchol".

The α-butylglucoside esters of fatty acid which may be used according to the invention are, preferably, either mixtures of α-butylglucoside esters of various fatty acids in which the various fatty chains contain, relative to each other, a similar number of carbon atoms (for example differing by 1 or 2), or mixtures of α-butylglucoside mono-, di-, tri- or polyesters of the same fatty acid.

The α-butylglucoside ester(s) of fatty acid used according to the invention preferably comprise a fatty chain having from 8 to 24 carbon atoms, more preferably from 12 to 22 carbon atoms, and even more preferably from 14 to 18 carbon atoms.

Mention may be made, for example, of α-butylglucoside esters of lauric ($C_{12}$), myristic ($C_{14}$), palmitic ($C_{16}$), stearic ($C_{18}$) and behenic ($C_{22}$) acid.

A mixture of α-butylglucoside mono- and diester of palmitic acid obtained according to the enzymatic manufacturing process described in accordance with the invention is used more particularly.

The α-butylglucoside esters of fatty acid which may be used in accordance with the invention may be prepared from α-butylglucoside obtained according to the enzymatic manufacturing process described in patent application FR-A-2,680,373, the disclosure of which is specifically incorporated herein by reference, which includes placing butanol in contact with starch, maltodextrins or maltose in the presence of a purified enzymatic preparation having α-transglucosylation activity.

The α-butylglucoside esters of fatty acid may be synthesized by reacting the fatty acid or the corresponding fatty acid mixture with α-butylglucoside according to standard esterification processes such as those using a lipase or an equivalent.

The lipid vesicles with an aqueous core in accordance with the invention preferably comprise a lipid-phase membrane formed from at least one fatty acid ester, as defined above, and from at least one ionic amphiphilic lipid.

The ionic amphiphilic lipids associated with the ester or with the mixture of fatty acid esters, used for the manufacture of the lipid vesicles of the invention, are preferably selected from:

(1) neutralized anionic lipids, these anionic lipids preferably being chosen from:
   alkaline salts of dicetyl phosphate and of dimyristyl phosphate, in particular the Na and K salts;
   alkaline salts of cholesteryl sulphate, in particular the Na salt;
   salts of lipoamino acids such as mono- and disodium acylglutamates;
   the sodium salt of phosphatidic acid;

(2) amphoteric lipids, these amphoteric lipids preferably being phospholipids, in particular pure soya phosphatidylethanolamine;

(3) alkylsulphonic derivatives, these derivatives preferably being the compounds of formula:

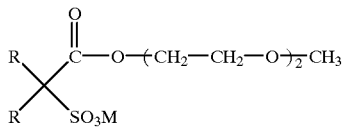

wherein each R independently represents $C_{12}$–$C_{22}$ radical, in particular a $C_{16}H_{33}$ and a $C_{18}H_{37}$ radical, taken as a mixture or separately, and M is an alkali metal, preferably sodium.

Preferably, the weight ratio between the amount of fatty acid ester and the amount of ionic amphiphilic lipid ranges from 50/1 to 50/25 and the weight ratio between the amount of lipid phase and the amount of aqueous phase ranges from 1/1000 to 300/1000.

The lipid vesicles with an aqueous core may be prepared by any known process for the manufacture of amphiphilic lipid vesicles and are more preferably prepared by the so-called "lipid co-fusion" process.

It is possible, in a known manner, to incorporate into the lipid phase constituting the lipid membrane of the vesicles at least one additive whose main function is to reduce the permeability of the vesicles, to prevent their flocculation and their fusion and to increase the degree of encapsulation.

According to the invention, at least one additive may be added to the lipid phase, this additive is preferably chosen from the group formed by:
   sterols, in particular phytosterols and cholesterol,
   long-chain alcohols and diols, and
   long-chain amines and quaternary ammonium derivatives thereof.

These additives may possibly have cosmetic and/or dermopharmaceutical activity. This is the case, for example, for cholesterol.

The vesicles of the compositions according to the invention may contain, in a known manner, one or more active agent(s) having a cosmetic and/or dermopharmaceutical activity, which, depending on their solubility properties, may have different localizations.

If the active agents are water-soluble, they are introduced into the encapsulated aqueous phase of the vesicles. If the active agents are liposoluble, they are introduced into the lipid phase constituting the membrane. If the active agents are amphiphilic, they distribute themselves between the lipid phase and the encapsulated aqueous phase, with a partition coefficient which varies depending on the nature of the amphiphilic active agent and the respective compositions of the lipid phase and of the encapsulated aqueous phase.

The water-soluble active agents preferably include glycerol, sorbitol, erythrulose and antibiotics. The liposoluble or partially liposoluble (amphiphilic) active agents are preferably chosen from those which do not significantly increase the permeability of the vesicles, do not bring about their flocculation and fusion and do not decrease the degree of encapsulation. Liposoluble active agents which also constitute additives may be advantageously used.

The preferred liposoluble active agents according to the invention are selected from:
   sphingomyelins,
   glycoceramides, in particular those obtained from wheatgerm, and
   natural or synthetic ceramides, preferably those described in French patent application No. 91/02091 filed on Feb. 21, 1991, the disclosure of which is specifically incorporated by reference herein having the formula:

wherein
   $R_1$ represents a $C_{11}$–$C_{21}$ alkyl or alkenyl radical,
   $R_2$ represents:
      a saturated $C_{11}$–$C_{23}$ hydrocarbon radical, or
      a mixture of saturated linear $C_{11}$–$C_{19}$ hydrocarbon radicals bearing at least one ethylenic unsaturation, preferably 1 or 2, in which the proportion of saturated radicals cannot exceed 35%;
the ceramide of formula (II) being in the form of a racemic mixture of erythro and threo diastereoisomers in erythro/threo proportions ranging from 85/15 to 60/40.

According to the invention, a mixture of ceramide(s) and cholesterol are preferably introduced into the lipid phase constituting the membrane. The reason for this is that the use of this mixture is particularly advantageous since it allows the lipids of the skin to be reconstituted when the vesicles in the dispersion according to the invention are degraded on the skin.

The dispersion in accordance with the invention preferably contains an oil dispersed in the aqueous phase by lipid vesicles having an aqueous core.

The oil may preferably be selected from:
   animal or plant oils formed by fatty acid esters of polyols, in particular liquid triglycerides, for example sunflower oil, corn oil, soya oil, marrow oil, grapeseed oil, jojoba oil, sesame oil, hazelnut oil, fish oils, glyceryl tricaprocaprylate, or plant or animal oils of formula $R_9COOR_{10}$, in which formula $R_9$ represents a higher fatty acid residue containing from 7 to 19 carbon atoms and $R_{10}$ represents a hydrocarbon chain containing from 3 to 20 carbon atoms, for example purcellin oil;
   natural or synthetic essential oils such as, for example, eucalyptus oil, hybrid lavender oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil;
   hydrocarbons, such as hexadecane and liquid paraffin;
   halocarbons, in particular fluorocarbons such as fluoroamines, for example perfluorotributylamine, fluorohydrocarbons, for example perfluorodecahydronaphthalene, fluoro esters and fluoro ethers;

silicones, for example polysiloxanes, polydimethylsiloxanes and fluorosilicones;

inorganic acid esters of an alcohol; and ethers and polyethers.

The dispersing aqueous phase may also contain water-soluble cosmetic and/or dermopharmaceutical active agents. The oil may optionally contain a liposoluble active agent.

The compositions according to the invention comprise uncoated inorganic pigments and/or organic pigments.

Among the organic pigments which may be mentioned are lakes such as D and C red No. 7 calcium lakes, D and C red Nos. 6 and 9 barium lakes, D and C red No. 3 and D and C yellow No. 5 aluminium lakes, and D and C orange No. 5 zirconium lakes.

Among the inorganic pigments which may be mentioned are (red, brown, black and yellow) iron oxides, chromium oxides, ultramarines (aluminosilicate polysulphides), manganese pyrophosphate and Prussian blue (ferric ferrocyanide), and titanium oxides.

The uncoated pigments are present in the compositions of the invention in proportions preferably ranging from 1 to 20% by weight, and more preferably from 2 to 12% by weight, relative to the total weight of the composition.

The compositions according to the invention may also contain in the aqueous phase matte-effect agents such as, for example, magnesium carbonate, starch or modified starches, polyethylene powder, zinc powder, zinc oxide, magnesium stearate, zinc stearate, silicone-containing resin microbeads such as the product sold under the name Tospearl by the company Toshiba, and silica microspheres.

The compositions according to the invention may also contain cosmetic or dermatological active agents such as vitamin A, vitamin E, vitamin A palmitate and vitamin F, and additives such as preserving agents, fragrances, sunscreens, antioxidants, bactericides, moisturizers, fillers such as talc, kaolin and mica, and gelling agents and dyes.

In the composition according to the invention, the vesicles generally have an average diameter ranging from 10 to 5000 nm. When the aqueous phase contains a dispersion of oil droplets, these droplets advantageously have an average diameter ranging from 100 to 10,000 nm.

Another subject of the invention is a process for dispersing a pulverulent inorganic filler and/or an organic filler in an oil-in-water dispersion of lipid vesicles, wherein the dispersion of lipid vesicles and the filler or fillers in the aqueous phase are mixed by means of a high-pressure homogenizing device in one or more mixing runs.

The high-pressure homogenizing devices used according to the invention are chosen in particular from those of Rannie®, Gaulin® or Soavie® type.

The pressures used preferably range from 400 to 800 bar (i.e., from 4 to $8 \times 10^7$ Pa) and more particularly from 450 to 600 bar (i.e., from 4.5 to $6 \times 10^7$ Pa). The temperature used is preferably room temperature.

The dispersion process in accordance with the invention makes it possible, unexpectedly, to finely and homogeneously disperse uncoated pigments acting as fillers in oil-in-water dispersions of lipid vesicles with an aqueous core in which the lipid membrane is formed from fatty acid esters as defined above.

The compositions in accordance with the present invention as defined above may be prepared according to a process comprising the following steps:

(a) an aqueous suspension of uncoated pigments is mixed with an oily dispersion of lipid vesicles with an aqueous core containing fatty acid esters, at room temperature;

(b) the mixture is homogenized according to a standard process for homogenizing an oil-in-water dispersion (turbomixer);

(c) a high-pressure homogenization is carried out according to the dispersion process as described above.

Preferably, the mixture obtained after each run of the mixture through the high-pressure homogenizer is cooled to room temperature by a current of cold air and is then deaerated.

Another subject of the invention is compositions for topical application comprising the compositions as defined above.

Another subject of the invention is the use of the compositions as defined above as a base for products to care for and/or make up the face and/or the body and/or the scalp.

The products obtained from the compositions of the invention may be cosmetic or dermopharmaceutical. They may be in the form of a relatively thickened dispersion, a gel, a cream, a milk or a serum. Among the make-up compositions which may be mentioned are foundations, tinted creams and complexion correctors or enhancers.

The invention also relates to a process for cosmetically treating the skin and/or the scalp, wherein a composition as defined above is applied to the skin or the scalp.

The examples below, given purely by way of illustration and with no limiting nature implied, will allow a better understanding of the invention to be gained.

In all the examples given below, the vesicle dispersions are prepared by the so-called "lipid co-fusion" process in which:

in a first phase, the lipid phase is prepared by mixing, in liquid form, various amphiphilic lipids of which it is composed, and is optionally combined with additives or liposoluble active agents, and the lipid phase obtained is placed in the presence of an aqueous phase optionally containing water-soluble active agents, so as to obtain a lamellar phase, and the mixture is then homogenized; and in a second phase, the mixture is stirred vigorously in a homogenizer in order to obtain vesicles dispersed in a dispersing aqueous phase.

EXAMPLES

Example 1

Foundation

| Phase $A_1$ | |
|---|---|
| Sorbitan palmitate marketed under the name Span 40 by the company ICI | 2.85 g |
| Cholesterol | 2.85 g |
| Monosodium glutamate marketed under the name "Acylglutamate HS11" by the company Ajinomoto | 0.3 g |
| Tocopherol | 1.1 g |
| Phase $A_2$ | |
| Demineralized water | 35 g |
| Glycerol | 3 g |
| Preserving agent | 0.1 g |
| Anhydrous citric acid | 0.02 g |
| Phase $B_1$ | |
| Phenyltrimethylsiloxysiloxane sold under the name "DC556 Fluid Cosmetic" by Dow Corning | 12 g |
| 2-Ethylhexyl palmitate sold under the name "Ceraphil 368" by the company van Dyk | 4 g |

-continued

| Phase B₂ | |
|---|---|
| Isostearyl neopentanoate sold under the name "Ceraphil 375" by the company van Dyk | 4 g |
| Preserving agent | 0.15 g |
| Phase C₁ | |
| Magnesium aluminium silicate sold under the name "Veegum" by the company Vanderbilt | 0.75 g |
| Demineralized water | 22.58 g |
| Phase C₂ | |
| Yellow iron oxide (uncoated pigment) | 0.98 g |
| Yellow iron oxide and brown iron oxide (uncoated pigments) | 0.58 g |
| Black iron oxide (uncoated pigment) | 0.2 g |
| Titanium oxide (uncoated pigment) | 5.24 g |
| Phase D | |
| Demineralized water | 1 g |
| Preserving agent | 0.3 g |
| Phase E | |
| Talc (filler) | 2 g |
| Phase F | |
| Gelling agent | 1 g |

Procedure

The lipid vesicles were melted at 90° C. (phase A₁). The melted product was hydrated with phase A₂, which had been prepared at 85° C. The mixture was cooled to 60° C. The mixture was passed twice through a high-pressure homogenizer at 500 bar and the dispersion of lipid vesicles obtained was cooled.

The fatty phase (B₁+B₂) was added to the dispersion and the oils were dispersed in the aqueous phase with the high-pressure homogenizer at 500 bar in 2 successive mixing runs.

An aqueous suspension of uncoated pigments was formed by dispersing phase C₂ in phase C₁ at 60° C. The mixture was cooled to room temperature. The dispersion of vesicles on the pigments was aspirated with a pump.

The mixture was passed through the high-pressure homogenizer in 2 successive mixing runs.

The mixture was cooled and deaerated. Phases D, E and F were then added and the final mixture was homogenized with a turbomixer.

Example 2
Foundation

| Phase A₁ | |
|---|---|
| Butylglucopyranoside palmitate | 2.7 g |
| Cholesterol | 2.7 g |
| Monosodium glutamate marketed under the name "Acylglutamate HS11" by the company Ajinomoto | 0.6 g |
| Phase A₂ | |
| Demineralized water | 40 g |
| Glycerol | 2 g |
| Preserving agent | 0.1 g |
| Phase B₁ | |
| Macadamia oil | 12 g |
| Preserving agent | 0.15 g |
| Phase B₂ | |
| Cyclopentadimethylsiloxane (4 cst) | 7.5 g |
| Glyceryl esters of essential fatty acids | 3.0 g |
| Preserving agent | 0.15 g |
| Phase C₁ | |
| Demineralized water | 17.95 g |
| Phase C₂ | |
| Yellow iron oxide (uncoated pigment) | 0.69 g |
| Yellow iron oxide and brown iron oxide (uncoated pigments) | 0.30 g |
| Black iron oxide (uncoated pigment) | 0.13 g |
| Titanium oxide (uncoated pigment) | 5.88 g |
| Phase D | |
| Demineralized water | 1 g |
| Preserving agent | 0.3 g |
| Phase E | |
| Gelling agent | 3 g |

The procedure was identical to that of Example 1.

Comparative Example 3 According to the Prior Art
Foundation

| Phase A₁ | |
|---|---|
| Sorbitan palmitate marketed under the name Span 40 by the company ICI | 2.85 g |
| Cholesterol | 2.85 g |
| Monosodium glutamate marketed under the name "Acylglutamate HS11" by the company Ajinomoto | 0.3 g |
| Tocopherol | 1.1 g |
| Phase A₂ | |
| Demineralized water | 35 g |
| Glycerol | 3 g |
| Preserving agent | 0.1 g |
| Anhydrous citric acid | 0.02 g |
| Phase B₁ | |
| Phenyltrimethylsiloxysiloxane sold under the name "DC55 Fluid Cosmetic" by Dow Corning | 12 g |
| 2-Ethylhexyl palmitate sold under the name "Ceraphil 368" by the company van Dyk | 4 g |
| Phase B₂ | |
| Isostearyl neopentanoate sold under the name "Ceraphil 375" by the company van Dyk | 4 g |
| Preserving agent | 0.15 g |
| Phase C | |
| Yellow iron oxide (coated pigment) | 0.98 g |
| Yellow iron oxide and brown iron oxide (coated pigments) | 0.58 g |
| Black iron oxide (coated pigment) | 0.2 g |
| Titanium oxide (coated pigment) | 5.24 g |
| Phase D | |
| Demineralized water | 1 g |
| Preserving agent | 0.3 g |
| Phase E | |
| Talc (filler) | 2 g |
| Phase F | |
| Gelling agent | 1 g |

Procedure

The lipid vesicles were melted at 90° C. (phase A₁). The melted product was hydrated with phase A₂ which had been prepared at 85° C. The mixture was cooled to 60° C. The mixture was passed twice through a high-pressure homogenizer at 500 bar and the dispersion of lipid vesicles obtained was cooled.

The fatty phase ($B_1+B_2$) was added to the dispersion and the oils were dispersed in the aqueous phase with the high-pressure homogenizer at 500 bar in 2 successive mixing runs.

The phases C (coated pigments), D, E and F were then added and the final mixture is homogenized with a turbo-mixer.

Comparison Between the Formulation of Example 1 and that of Comparative Example 3

The presence or absence of lumps of pigments and the quality of the emulsion were studied with a G×100 optical microscope.

| EXAMPLE 1 (invention): | Fine and homogeneous. No lumps of pigments. |
|---|---|
| COMPARATIVE EXAMPLE 3: (prior art) | Less fine and less homogeneous Lumps of pigments larger than or equal to 40 μm in size. |

What is claimed is:

1. A composition comprising an aqueous dispersion, said aqueous dispersion comprising an aqueous phase having dispersed within it:
   (a) one or more uncoated pigments; and
   (b) lipid vesicles having an aqueous core and a membrane formed from at least one fatty acid ester, wherein said one or more uncoated pigments are in said aqueous phase and not within said aqueous core of said lipid vesicles.

2. A composition according to claim 1, wherein said aqueous dispersion is an oil-in-water dispersion and wherein said lipid vesicles act as an agent for dispersing droplets of at least one oil in said aqueous phase of said oil-in-water dispersion.

3. A composition according to claim 1, wherein said at least one fatty acid ester forming said membrane of said lipid vesicles is:
   a) a polyoxyethylenated or non-polyoxyethylenated polyol ester of fatty acid; or
   b) a α-butylglycoside ester of fatty acid.

4. A composition according to claim 3, wherein said polyol ester of fatty acid is selected from a mixture of esters of at least one polyol and at least one fatty acid,
   wherein said at least one polyol is selected from:
      a) polyethylene glycol comprising from 1 to 60 ethylene oxide units;
      b) sorbitan;
      c) sorbitan comprising from 2 to 60 ethylene oxide units;
      d) glycerol comprising from 2 to 30 ethylene oxide units;
      e) polyglycerols comprising from 2 to 15 glycerol units;
      f) sugars; and
      g) glucoses comprising from 2 to 30 ethylene oxide units, and
   said at least one fatty acid comrises a $C_5$–$C_{17}$ alkyl chain, wherein said alkyl chain is linear or branched, saturated or unsaturated, and wherein the number of alkyl chains per polyol group ranges from 1 to 10.

5. A composition according to claim 3, where said α-butylglycoside ester of fatty acid comprises a fatty chain having from 8 to 24 carbon atoms.

6. A composition according to claim 3, wherein said α-butylglycoside ester of fatty acid is a mixture of α-butylglycoside esters of fatty acids in which the fatty chains contain, relative to each other, a similar number of carbon atoms.

7. A composition according to claim 3, wherein said α-butylglycoside ester of fatty acid is a mixture of α-butylglycoside esters selected from mono-, di-, tri-, and polyesters of the same fatty acid.

8. A composition according to claim 5, wherein said fatty chain has from 12 to 22 carbon atoms.

9. A composition according to claim 8, wherein said fatty chain has from 14 to 18 carbon atoms.

10. A composition according to claim 7, wherein said α-butylglycoside ester of fatty acid is a mixture of α-butylglycoside monoester and α-butylglycoside diester of palmitic acid.

11. A composition according to claim 1, wherein said lipid vesicles comprise a membrane formed from at least one fatty acid ester and at least one ionic amphiphilic lipid.

12. A composition according to claim 11, wherein said at least one ionic amphiphilic lipid is selected from:
   a) alkaline salts of dicetyl phosphate and dimyristyl phosphate;
   b) alkaline salts of cholesteryl sulphate;
   c) alkaline salts of lipoamino acids;
   d) the sodium salt of phosphatidic acid;
   e) phospholipids; and
   f) alkylsulphonic derivatives of the formula:

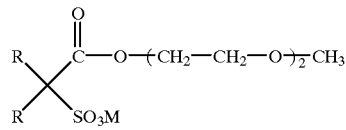

wherein each R independently represents a $C_{12}$–$C_{22}$ radical and M represents an alkali metal.

13. A composition according to claim 12, wherein each R independently represents a $C_{16}H_{33}$ or $C_{18}H_{37}$ radical.

14. A composition according to claim 12, wherein M represents sodium.

15. A composition according to claim 11, wherein said at least one fatty acid ester and said at least one ionic amphiphilic lipid are present in a weight ratio ranging from 50/1 to 50/25, and wherein said lipid phase and said aqueous phase are present in a weight ratio ranging from 1/1000 to 300/1000.

16. A composition according to claim 1, wherein said membrane of said lipid vesicles additionally comprises at least one additive.

17. A composition according to claim 16, wherein said at least one additive is selected from sterols, long-chain alcohols, long-chain diols, long-chain amines and quaternary derivatives of long-chain amines.

18. A composition according to claim 17, wherein said at least one additive is selected from phytosterols and cholesterol.

19. A composition according to claim 18, wherein said at least one additive is cholesterol.

20. A composition according to claim 1, wherein said lipid vesicles additionally comprise at least one active agent selected from cosmetic active agents and dermopharmaceutically active agents.

21. A composition according to claim 1, wherein said membrane of said lipid vesicles additionally comprises at least one lipophilic active agent.

22. A composition according to claim 1, wherein the aqueous core of said lipid vesicles encapsulates at least one water-soluble active agent.

23. A composition according to claim 1, wherein said lipid vesicles additionally comprise at least one amphiphilic active agent distributed between said membrane and said aqueous core.

24. A composition according to claim 21, wherein said at least one lipophilic active agent is selected from sphingomyelins, glycoceramides, natural ceramides and synthetic ceramides.

25. A composition according to claim 1, wherein said membrane additionally comprises a mixture of at least one ceramide and cholesterol.

26. A composition according to claim 1, wherein at least one oil is dispersed by said lipid vesicles in said aqueous phase.

27. A composition according to claim 26, wherein said at least one oil is selected from animal oils, plant oils, natural essential oils, synthetic essential oils, hydrocarbons, halocarbons, silicones, inorganic acid esters of an alcohol, ethers and polyethers.

28. A composition according to claim 26, wherein said at least one oil comprises at least one liposoluble active agent.

29. A composition according to claim 1, wherein said one or more uncoated pigments dispersed in said aqueous phase are present in a concentration ranging from 1 to 20% by weight, relative to the total weight of the composition.

30. A composition according to claim 1, wherein said one or more uncoated pigments dispersed in said aqueous phase are present in a concentration ranging from 2 to 12% by weight, relative to the total weight of the composition.

31. A composition according to claim 1, wherein said aqueous dispersion additionally comprises at least one additive selected from matte-effect agents, fillers, preserving agents, gelling agents, dyes, water-soluble cosmetic agents, liposoluble cosmetic agents, water-soluble dermatological active agents and liposoluble dermatological active agents.

32. A composition according to claim 1, wherein said lipid vesicles have an average diameter ranging from 10 to 5000 nm.

33. A composition according to claim 2, wherein said oil droplets have an average diameter ranging from 100 to 10,000 nm.

34. A composition according to claim 1, wherein said composition is a cosmetic or dermatological composition.

35. A composition according to claim 34, wherein said composition is a base for products selected from body-care products, face make-up products, facial-care products and scalp-care products.

36. A composition according to claim 35, wherein said composition is in a form selected from a thickened dispersion, a gel, a cream, a milk and a serum.

37. A composition according to claim 35, wherein said face make-up products are selected from foundations, tinted creams, complexion correctors and complexion enhancers.

38. A process for cosmetically treating the skin, the scalp or both, which comprises the step of applying a cosmetically effective amount of a composition according to claim 34 to the skin, the scalp or both.

* * * * *

UNITED STATES PATENT AND TRADEMARK OFFICE
CERTIFICATE OF CORRECTION

PATENT NO. : 5,972,378
DATED : October 26, 1999
INVENTOR(S) : TERREN et al.

It is certified that error appears in the above-identified patent and that said Letters Patent is hereby corrected as shown below:

Claim 30, col. 13, line 26, change "claim 1" to --claim 29--.

Signed and Sealed this

Sixteenth Day of May, 2000

*Attest:*

Q. TODD DICKINSON

*Attesting Officer*     *Director of Patents and Trademarks*